United States Patent [19]

Godfroid et al.

[11] 4,399,299
[45] Aug. 16, 1983

[54] BIS(SUBSTITUTED PHENOXYACETATES) OF N-ALKYL-DIALCANOLAMINES AND PHARMACEUTICAL COMPOSITIONS THEREOF

[75] Inventors: Jean-Jacques Godfroid; Jean Thuillier, both of Paris, France

[73] Assignee: Agence Nationale de Valorisation de la Recherche (ANVAR), Paris, France

[21] Appl. No.: 256,167

[22] Filed: Apr. 21, 1981

[30] Foreign Application Priority Data

Apr. 3, 1980 [FR] France ................ 80 09886

[51] Int. Cl.³ ............................................. C07C 69/76
[52] U.S. Cl. .................................... 560/63; 424/308; 424/309
[58] Field of Search .................. 560/63; 424/308, 309

[56] References Cited

U.S. PATENT DOCUMENTS 3,494,957 2/1970 Nakanishi et al. ................ 560/63

Primary Examiner—Paul J. Killos
Attorney, Agent, or Firm—Hammond & Littell, Weissenberger and Muserlian

[57] ABSTRACT

The invention relates to bis(substituted phenoxyacetates) of N-alkyl-dialkanolamines.

These compounds are of the formula:

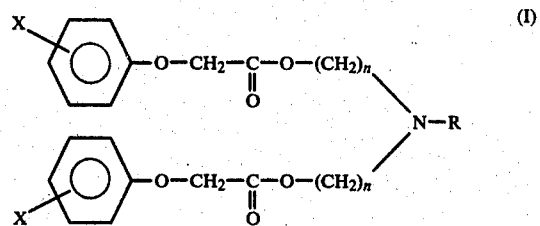

wherein:
X is chlorine, fluorine or trifluoromethyle,
n is in the range from 1 to 3 and is preferably 2,
R is a lower alkyl group, such as methyl or ethyl group, and the pharmaceutically acceptable salts of said compounds.

Application: prevention and treatment of cerebral disorders.

16 Claims, No Drawings

BIS(SUBSTITUTED PHENOXYACETATES) OF N-ALKYL-DIALCANOLAMINES AND PHARMACEUTICAL COMPOSITIONS THEREOF

The present invention relates to bis(substituted phenoxyacetates) of N-alkyl-dialkanolamines, a method for their obtention and their applications as medicaments.

There are already known substituted phenoxyacetate derivatives having pharmacological properties, in particular dimethylaminoethyl 4-chloro-phenoxyacetate, which is currently called "Meclofenoxate." This compound, which is used as a central metabolism regulator, was described in FR Pat. No. 1 359 614 and in "special medicament" FR Pat. No. 398 M.

There are also known other esters of aryloxyalkanoic acids. In this connection, mention may be made of U.S. Pat. No. 2 771 477, relating to low volatile herbicidal compositions containing as the active ingredients esters of aryloxyalkane-carboxylic acid with alkanolamines which have at least one free hydroxy group.

BE Pat. No. 674 556 relates to polyol esters of alpha-aryloxy-alcanoic acids suitable for the treatment of hypercholesterinemia.

FR Pat. No. 70.13 346, published under No. 2 085 634, relates to polyfunctional esters of 2-(p-chlorophenoxy) 2-methyl-propionic acid and their use as medicaments exhibiting hypolipemic and hypocholesterolemic activity.

It will be noted that the products having hypocholesterolemic properties described in those references have a highly lipophilic aromatic structure. These products are so lipophilic that they cannot get through the haemato encephalic wall.

There has now been found a new series of chemical compounds, which are stimulators of the central nervous activity, apt to counteract disorders of the nervous cell and of its metabolism. These compounds also have an effect against plaquette-aggregation and a diuretic effect.

The compounds according to the present invention are bis(substituted phenoxyacetates) of N-alkyl-dialkanolamines, which are represented by the following general formula:

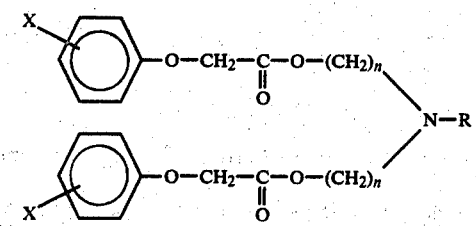

wherein:

X is chlorine, fluorine or trifluoromethyle,
n is in the range of 1 to 3 and is preferably 2,
R is a lower alkyl group, such as methyl or ethyl group.

The invention also relates to the pharmaceutically acceptable salts of compounds of formula I.

The invention also has for its object a method for the obtention of the compounds of formula I. This method consists:

1. in reacting, the phenoxyacetic acid of formula:

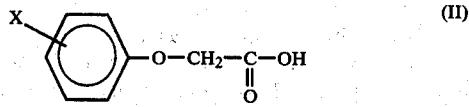

or a derivative thereof, with a N-alkyl-dialkanolamine of the formula:

in an acid to alcohol ratio substantially of 2:1, X, R and n being such as defined above, 2. in converting, if so required, the thus obtained compound into a pharmaceutically acceptable salt.

As derivatives of the acid, use may be made of the ester, the acid chloride or the anhydride.

Advantageously, there is used the chloride of the phenoxyacetic acid of formula II in a suitable aliphatic or aromatic solvent, e.g. benzene, with solvent reflux. The product resulting from the reaction of this acid chloride with the amine of formula III is therefore a hydrochloride which may be converted by conventional means into the corresponding free amine, for instance by reaction with sodium carbonate. The free amine thus obtained may thereafter be converted into a pharmaceutically acceptable salt by reaction with an acid under conventional conditions. Suitable acids are maleic acid, fumaric acid, oxalic acid, succinic acid, citric acid, methane-sulfonic acid and the like.

The particularly preferred compound according to the invention is the N-methyl-diethanolamine bis-(4-chloro-phenoxyacetate).

The compounds according to the invention have a remarkable action on cerebral physiology and in particular on the diencephalic and hypothalamic regions.

Tests made with the N-methyl-diethanolamine bis(4-chloro-phenoxyacetate) indeed showed that the same counteracts cerebral oedemas and disorders caused by hypocapine. It improves the cerebral metabolism by action on the nervous cells. Its action may be checked by tests involving the hypothalamus physiology, the chromatophore stimulation and modifications in the hunger and thirst behaviours.

In experimental procedures, the N-methyl-diethanolamine bis(4-chlorophenoxyacetate) proved to be 2 to 10 times more active than "Meclofenoxate" which, in turn, proved to be ineffective in certain tests where the preferred compound according to the invention was highly effective.

The present invention also relates to the therapeutical application of the compounds of formula (I) in the field of prevention and treatment of cerebral disorders in intoxications and comas, vascular accidents and derangements of the diencephalohypothalamo-hypophysis functions.

Finally, the invention related to pharmaceutical compositions containing as the active ingredient a compound of formula I in combination with a pharmaceutically acceptable carrier.

The pharmaceutically acceptable carrier is selected among the conventional carriers of current use in the field of medicaments. It should be inert with respect to the compounds of the invention.

The pharmaceutical compositions according to the invention may be under the form of compositions for buccal or parenteral administration.

The particularly preferred pharmaceutical compositions contain 0.05 g to 1.50 g of N-methyl-diethanolamine bis-(4-chloro-phenoxyacetate).

The invention will be now illustrated by no way of limitation by the following examples:

EXAMPLE 1

Preparation of the N-methyl-diethanolamine bis-(4-chloro-phenoxyacetate)

128 g of parachlorophenoxyacetic acid chloride were poured dropwise into a mixture of 30 g of freshly distilled N-methyl-diethanolamine in 100 cm³ of benzene. The mixture was then brought to benzene reflux, with strong stirring during two hours. After cooling down to ordinary temperature, the hydrochloride crystals of the sought compound were dried, successively washed with anhydrous ether and with lukewarm acetone.

After drying at about 100° C. under vacuum, there was obtained 96 g of the hydrochloride of the sought product having a melting point MP=145°-146° C. (capillary method) Yield: 84%. This product can be recrystallized in ethanol or isopropanol. It exists under a second cristalline form, the melting point (Köpfler) thereof being 116°-120° C.

The salt obtained was a white powder insoluble in ether and acetone and soluble in lukewarm water.

| Analysis: $C_{21}H_{24}Cl_3NO_6$ | | | | |
|---|---|---|---|---|
| | C | H | N | Cl |
| Calculated: | 51.32 | 4.88 | 2.85 | 21.38 |
| Found: | 51.61 | 4.85 | 2.85 | 21.27 |

Infrared: ester band at 1730 cm$^{-1}$.

NMR, δ (ppm): 2.86, singlet $CH_3-N^+$, and 4.93, $O-CH_2-CO-$

Mass spectrography: molecular ion M$^+$ at 454 (molecular weight H-HCl)

Preparations of salts of PM 198 and obtention of the PM 198 base

The hydrochloride obtained above was taken up with soda or aqueous sodium carbonate. The aqueous phase was extracted with ether, the organic solution was washed with water, then said solution was dried. Subsequent evaporation was effected to obtain the PM 198 base.

The PM 198 base was taken up in a minimum amount of acetone, and a stoechiometric amount of methane sulfonic acid was poured. The PM 198 methane sulfonate then precipitated. The same was dried and recrystallized in methanol or ethanol.

After two recrystallizations in methanol, the PM 198 methane sulfonate had a melting point of 133° C. (Köpfler).

The analysis of this methane sulfonate was as follows:

| | Analysis | | | |
|---|---|---|---|---|
| | C | H | N | Cl |
| Calculated: | 49.43 | 4.15 | 2.50 | 6.34 |
| Found: | 49.53 | 4.06 | 2.54 | 6.29 |

The same procedure as above was adopted to prepare the maleate and the oxalate of PM 198 which had the following melting points after recrystallization in ethanol.

Maleate: 111° C. (Köpfler)
Oxalate: 137° C. (Köpfler)

It will be noted that the PM 198 base may be directly obtained by adding, in the mixture of parachlorophenoxyacetic acid chloride (2 moles)-N-methyl-diethanolamine (1 mole)-benzene, two moles of a proton-capture base, e.g. triethylamine or pyridine. The hydrochloride of these bases will then precipitate in the reaction medium.

EXAMPLE 2

The same procedure as in Example 1 was adopted to prepare the N-methyl-diethanolamine bis-(3-trifluoromethylphenoxyacetate) of the formula:

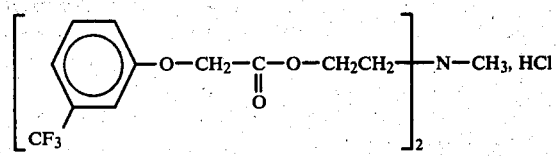

PM 240

MP=96° (Köpfler), recrystallization solvent: isopropyl alcohol/ligroin.

| | Analysis: | | | |
|---|---|---|---|---|
| | C | H | N | Cl |
| Calculated: | 49.43 | 4.15 | 2.50 | 6.34 |
| Found: | 49.53 | 4.06 | 2.54 | 6.29 |

EXAMPLE 3

Pharmacological Tests

The N-methyl-diethanolamine bis(4-chloro-phenoxyacetate) obtained according to Example 1 was subjected to different pharmacological and toxicological tests.

Due to the chemical analogy thereof with dimethylaminoethyl 4-chloro-phenoxyacetate (Meclofenoxate, of the formula):

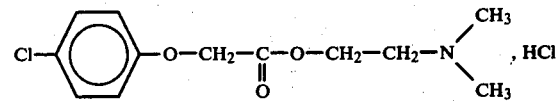

comparative tests were effected with these two compounds.

The N-methyl-diethanolamine bis(4-chloro-phenoxyacetate) hydrochloride according to the invention will be designated hereinafter, for the sake of simplification, by the abbreviation "PM 198".

TEST A

Toxicity of N-methyl-diethanolamine bis(4-chlorophenoxyacetate) and of Meclofenoxate The toxicities were studied in mice under oral and intra-veinous administration.

The toxicity calculations were effected according to LICHTFIELD and WILCOXON's method (J. Pharm. and Exp. Therap. 1949-95. p. 99,115).

| Products | DL 50 P.O. mg/kg | DL 50 I.V. mg/kg |
|---|---|---|
| Meclofenoxate | 1750 | 400 |
| PM 198 | 1750 | 435 |

P.O.: administration per os
I.V.: intra-veinous administration.

The two compounds have substantially the same toxicities.

TEST B

Action of the central nervous system

I. Action on the brain

1. Test with triethyltin

The alkylated compounds of tin are toxic and will cause selective oedema of the central nervous system and especially of the brain [KATZMAN et al. Arch. Neurol. 9, 178, 1963]. These alkylated compounds of tin will increase the water content of the cerebral tissue. Similarly, the cerebral sodium content is increased while the potassium is decreased.

It was found that at a dose of 50 mg per kg, PM 198 will reduce cerebral oedema in rats treated with triethyltin. By contrast, 100 mg/kg of "Meclofenoxate" are required to provide the same result.

Moreover, it was noted that PM 198 is much more effective on the neurologic syndroma than Meclofenoxate, the rats retaining a behaviour much closer to the normal one.

2. Test of repetitive electroshocks in rats

Electroshocks successively effected in rats and repeated three times at 20-minute intervals result in cerebral metabolism disorders characterized by a loss of the orientation reflexes and a defective response to painful stimuli.

A preventive treatment using administration of PM 198 60 minutes before the first electroshock allowed the obtention of a highly effective protection with respect to this test.

Indeed, it was found that intra-gastric administration of 100 mg/kg of PM 198 significantly improved the orientation response as from the first electroshock.

Upon the second and third electroshocks, the orientation indices are still higher and in a significant manner than those of the reference animals (P=0.01).

Meclofenoxate, even at a dose of 200 mg/kg remains absolutely inactive for this test.

3. Action of PM 198 on the cerebral pain syndroma caused in dogs by hyperventilation entailing hypocapnia Hypocapnia provoked in dogs involves a cerebral pain which is measured:
- by studying the oxygen availability,
- by the arterio-veinous difference in oxygen,
- by the oxygen consumption per minute.

Also studied are the perfusion pressure and the cerebral vascular resistance as per the ratio:

$$C.V.R. = \frac{\text{Systolic pressure}}{\text{Flow-rate l/minute}}$$

PM 198, at a dose of 50 mg/kg in I.V. perfusion to dogs over 20 minutes, counteracted, during one hour, any variation of the cerebral veinous flow-rate.

The veinous oxygen pressure remained normal and the oxygen consumption increased. There occurred no decompensation.

Meclofenoxate, at a dose of 50 mg/kg I.V., counteracted, but only for 20 minutes, the decrease in the cerebral blood flow-rate, but failed to maintain the oxygen pressure in the cerebral cortex. Decompensation occurred.

II—Action on the diencephalon

1. Action on fish chromatophores

The physiology of fish chromatophores is dependent on hypothalamic secretions of the lower portion of the diencephalon. Psychotropic and cerebral orientation drugs can modify the physiology of these regions [J. Thuillier et al. C.R. Soc. Biol. 1961, 155, 10 p. 1924–1928]. This test is known to demonstrate the action of the products on the diencephalon which controls distension and blackening of the fish chromatophores.

Use was made of Phoxinus Phoxinus Linné as immersed in an aquarium containing a selected concentration of PM 198. The time for the blackening of the fish to occur was measured. The same test was effected with Meclofenoxate. The results obtained are shown in Table I hereunder.

TABLE I

| Product | Concentration in the water | Minimum blackening time seconds |
|---|---|---|
| PM 198 | 0.01 per 1000 | 90 |
|  | 0.05 per 1000 | 45 |
|  | 0.10 per 1000 | 25 |
| Meclofenoxate | 0.05 per 1000 | nothing |
|  | 0.10 per 1000 | nothing |
|  | 0.25 per 1000 | 90 |

As from a concentration of 0.01 per 1000, PM 198 caused a blackening in Phoxinus Phoxinus Linné, while a 25 times larger dose was required to provide the same result with Meclofenoxate.

2. Action on hunger behaviours

Regulation of hunger and thirst is dependent on secreting stimulations from the hypothalamus. These regulator centers may be disturbed either in acquired manner in genetically obese animals, or consequent to the destruction of the involved centers by selective poisons such as aurothioglucose.

The action of PM 198 was studied in 2 types of hyperphagic obese mice, whereof some were genetically obese, the other being intoxicated by aurothioglucose.

2-1 Action of PM 198 on mice made hyperphagic with aurothioglucose

Administration of 250 mg/kg of aurothioglucose to mice cause bulimia with stomach distension and a steady increase in the weight of the animal as compared to reference animals. The results obtained are shown in Table II hereunder.

TABLE II

Action of PM 198 on the stomach weight

| Products | Dose mg/kg P.O. | Decrease in the stomach weight Test t. statistics | |
|---|---|---|---|
| | | As compared to the aurothioglucose references | Degree of significance |
| PM 198 | 100 | t = 2.3847 | P < 0.05 |
| | 150 | t = 2.3126 | P < 0.05 |
| Meclofenoxate | 250 | t = 2.2495 | P < 0.05 |

The results in Table II show that at a dose of 100 mg/kg, PM 198 caused a significant decrease in the stomach weight of mice treated with aurothioglucose. To provide the same result, a dose of 250 mg/kg of Meclofenoxate was required.

There was also measured the respective weight increases of mice treated and not treated with PM 198 and Meclofenoxate. The results obtained are shown in Table III hereunder:

TABLE III

Action of PM 198 on the development of aurothioglucose-induced obesity

| Product 100 mg/kg | Initial weight | Weight after 15 days | Weight increase | Weight increase in % |
|---|---|---|---|---|
| Absolute reference | 199 | 24.89 | 5.89 | 30% |
| Aurothioglucose reference | 219 | 32.85 | 11.85 | 57% |
| PM 198 | 20.38 | 27.75 | 7.37 | 36% |
| Meclofenoxate | 20.00 | 30.2 | 10.8 | 54% |

At a dose of 100 mg/kg, PM 198 reduced the gain in weight and counteracted aurothioglucose-induced obesity. At the same dose, Meclofenoxate was uneffective.

2-2 Action of PM 198 on genetical obesity in mice

There exists obese mice species (Elevage du Centre National de la Recherche Scientifique, Orléans).

PM 198 was administered gastrically for 12 consecutive days at a dose of 200 mg/kg to obese mice 14-weeks old.

The results showed a loss in weight of 4.027 g, i.e. 10.75%, and the aliment consumption of the animals treated was markedly reduced, by 35.4%.

Meclofenoxate, at a dose of 200 mg/kg, was poorly effective (decrease in weight of 2.2%).

TEST C

Anti-plaquette aggregation effect

PM 198, at a dose of 10 mg/kg, is active to counteract plaquette aggregation observed on pia-mater vessels. [M.M.G. BOZEIX, Int. Congress of Pharmacology, Paris, July 1978].

TEST D

Diuretic activities

At a dose of 100 mg/kg P.O., PM 198 caused an urinary excretion of the hydric overload of 37.7% over 6 hours.

We claim:

1. A compound selected from the group consisting of N-alkyl-dialkanolamine-bis-(substituted phenoxyacetate) of the formula

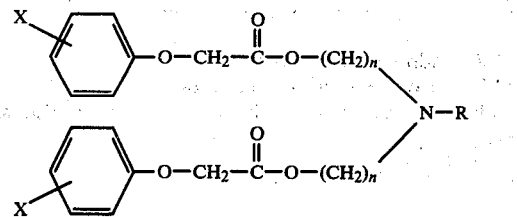

wherein X is selected from the group consisting of chlorine, fluorine and $-CF_3$, n is an integer from 1 to 3, R is lower alkyl and their non-toxic, pharmaceutically acceptable acid addition salts.

2. A compound of claim 1 wherein R is methyl or ethyl.

3. A compound of claim 1 or 2 wherein n is 2.

4. A compound of claim 1 selected from the group consisting of N-methyl-diethanolamine-bis-(4-chlorophenoxy-acetate) and N-methyl-diethanolamine-bis-(3-trifluoromethylphenoxy-acetate) and their non-toxic, pharmaceutically acceptable acid addition salts.

5. A compound of claim 4 wherein the acid addition salt is selected from the group consisting of hydrochloride, oxalate, maleate and methanesulfonate.

6. A compound of claim 1 which is the methanesulfonate of N-methyl-diethanolamine-bis-(4-chlorophenoxyacetate).

7. A composition for treatment or prevention of ceberal disorders comprising an amount of a compound of claim 11 sufficient to prevent or treat ceberal disorders and a pharmaceutical carrier.

8. A composition of claim 7 wherein R is methyl or ethyl.

9. A composition of claim 7 or 8 wherein n is 2.

10. A composition of claim 7 wherein the active compound is selected from the group consisting of N-methyl-diethanolamine-bis-(4-chlorophenoxyacetate) and N-methyl-diethanolamine-bis-(3-trifluoromethylphenoxyacetate) and their non-toxic, pharmaceutically acceptable acid addition salts.

11. A composition of claim 7 wherein the active compound is the methanesulfonate of N-methyl-diethanolamine-bis-(4-chlorophenoxyacetate).

12. A method of treating or preventing ceberal disorders in warm-blooded animals comprising administering to warm-blooded animals an amount of a compound of claim 1 sufficient to prevent or treat ceberal disorders.

13. The method of claim 12 wherein R is methyl or ethyl.

14. The method of claim 12 or 13 wherein n is 2.

15. The method of claim 12 wherein the compound is selected from the group consisting of N-methyl-diethanolamine-bis-(4-chlorophenoxyacetate) and N-methyl-diethanolamine-bis-(3-trifluoromethylphenoxyacetate) and their non-toxic, pharmaceutically acceptable acid addition salts.

16. The method of claim 12 wherein the compound is the methanesulfonate of N-methyl-diethanolamine-bis-(4-chlorophenoxyacetate).

UNITED STATES PATENT AND TRADEMARK OFFICE
CERTIFICATE OF CORRECTION

PATENT NO. : 4,399,299
DATED : August 16, 1983
INVENTOR(S) : JEAN-JACQUES GODFROID ET AL.

It is certified that error appears in the above-identified patent and that said Letters Patent is hereby corrected as shown below:

Column 8, lines 1, 2 and 3 of Claim 7;
Column 8, lines 1 and 4 of Claim 12:
        "ceberal" should read -- cerebral --.
Column 5, line 54: "pain syndroma" should read -- injury --.
Column 5, line 59: "pain" should read -- disease --.
Column 5, line 63: After "pressure" insert
        -- of the cerebral blood flow --.

Signed and Sealed this

Thirty-first Day of January 1984

[SEAL]

Attest:

GERALD J. MOSSINGHOFF

*Attesting Officer*     *Commissioner of Patents and Trademarks*